United States Patent [19]
Jin et al.

[11] Patent Number: 6,153,217
[45] Date of Patent: Nov. 28, 2000

[54] NANOCOCHLEATE FORMULATIONS, PROCESS OF PREPARATION AND METHOD OF DELIVERY OF PHARMACEUTICAL AGENTS

[75] Inventors: Tuo Jin; Leila Zarif, both of Newark; Raphael Mannino, Annandale, all of N.J.

[73] Assignees: Biodelivery Sciences, Inc.; University of Medicine and Denistry of New Jersey, both of Newark, N.J.

[21] Appl. No.: 09/235,400

[22] Filed: Jan. 22, 1999

[51] Int. Cl.[7] .............................. A61K 9/127; A61K 9/00
[52] U.S. Cl. ......................... 424/450; 424/400; 424/427; 424/430; 424/434; 424/435; 424/436; 436/829; 514/966; 514/967
[58] Field of Search .................................... 424/450, 400, 424/417, 427, 430, 434, 435, 436, 94.3, 1.21, 9.321, 9.51; 428/402.2; 935/54; 516/966, 9.67; 264/4.1, 4.3

[56] References Cited

U.S. PATENT DOCUMENTS

| | | | |
|---|---|---|---|
| 4,871,488 | 10/1989 | Mannino | 264/4.6 |
| 4,990,291 | 2/1991 | Schoen | 264/4.7 |
| 5,269,979 | 12/1993 | Fountain | 264/4.6 |
| 5,643,574 | 7/1997 | Gould et al. | 424/184.1 |
| 5,994,318 | 11/1999 | Gould et al. | 514/44 |

*Primary Examiner*—Gollamudi S. Kishore
*Attorney, Agent, or Firm*—Sughrue, Mion, Zinn, Macpeak & Seas, PLLC

[57] ABSTRACT

A process for producing a small-sized, lipid-based cochleate is described. Cochleates are derived from liposomes which are suspended in an aqueous two-phase polymer solution, enabling the differential partitioning of polar molecule based-structure by phase separation. The liposome-containing two-phase polymer solution, treated with positively charged molecules such as $Ca^{2+}$ or $Zn^{2+}$, forms a cochleate precipitate of a particle size less than one micron. The process may be used to produce cochleates containing pharmaceutical agents or biologically relevant molecules. Small-sized cochleates may be administered orally or through the mucosa to obtain an effective method of treatment.

26 Claims, 9 Drawing Sheets

NANOCOCHLEATE FORMULATIONS, PROCESS OF PREPARATION AND METHOD OF DELIVERY OF PHARMACEUTICAL AGENTS

FIELD OF THE INVENTION

The present invention relates to a novel process for preparing a novel lipid-based cochleate delivery system, the pharmaceutical preparations derived from the lipid-based cochleate delivery system, and the use of these pharmaceutical preparations to achieve efficient systemic and mucosal delivery of pharmaceutical agents.

BACKGROUND OF THE INVENTION

The ability of drugs to be administered via the oral route depends on several factors. The drug must be soluble in the gastrointestinal fluids in order for the drug to be transported across biological membranes for an active transport mechanism, or have suitable small particle size that can be absorbed through the Peyer's Patches in the small intestine and through the lymphatic system. Particle size is an important parameter when oral delivery is to be achieved (see Couvreur P. et al, Adv. Drug Delivery Reviews 10:141–162, 1993).

The primary issue in the ability to deliver drugs orally is the protection of the drug from proteolytic enzymes. An ideal approach is to incorporate the drug in a hydrophobic material so that the aqueous fluids cannot penetrate the system. Lipid-based cochleates are an ideal system that can achieve this purpose.

The advantages of cochleates are numerous. The cochleates have a nonaqueous structure and therefore they:

a) are more stable because of less oxidation of lipids;
b) can be stored lyophilized which provides the potential to be stored for long periods of time at room temperatures, which would be advantageous for worldwide shipping and storage prior to administration;
c) maintain their structure even after lyophilization, whereas liposome structures are destroyed by lyophilization;
d) exhibit efficient incorporation of hydrophobic drugs into the lipid bilayer of the cochleate structure;
e) exhibit efficient incorporation of antigens with hydrophobic moieties into the lipid bilayer of the cochleate structure;
f) have the potential for slow release of a drug, antigen or biologically relevant molecule in vivo as cochleates dissociate;
g) have a lipid bilayer which serves as a carrier and is composed of simple lipids which are found in animal and plant cell membranes, so that the lipids are non-toxic;
h) are produced easily and safely;
i) can be produced as defined formulations composed of predetermined amounts and ratios of drugs or antigens.

Cochleate structures have been prepared first by D. Papahadjopoulos as an intermediate in the preparation of large unilamellar vesicles (see U.S. Pat. No. 4,078,052). The use of cochleates to deliver protein or peptide molecules for vaccines has been disclosed in U.S. Pat. No. 5,840,707. However, neither of these patents addresses the importance of particle size or the effective oral delivery of drug mediated by small-sized cochleates.

SUMMARY OF THE INVENTION

Accordingly, it is an object of this invention to provide a method for obtaining a hydrogel-isolated cochleate of a particle size less than one micron. The method further comprises the steps required to encochleate at least one drug or biologically relevant molecule in the hydrogel-isolated cochleates in a therapeutically effective amount.

These and other objects have been obtained by providing a drug-cochleate, wherein said drug cochleate comprises the following components:

a) a drug component,
b) a negatively charged lipid, and
c) a divalent cation component, wherein the particle size of the drug cochleate is less than one micron.

The present invention further provides a method of orally administering to a host a biologically effective amount of the above-described drug-cochleate.

In a preferred embodiment, the drug-cochleate is administered orally.

DETAILED DESCRIPTION OF THE INVENTION

Figure 1:
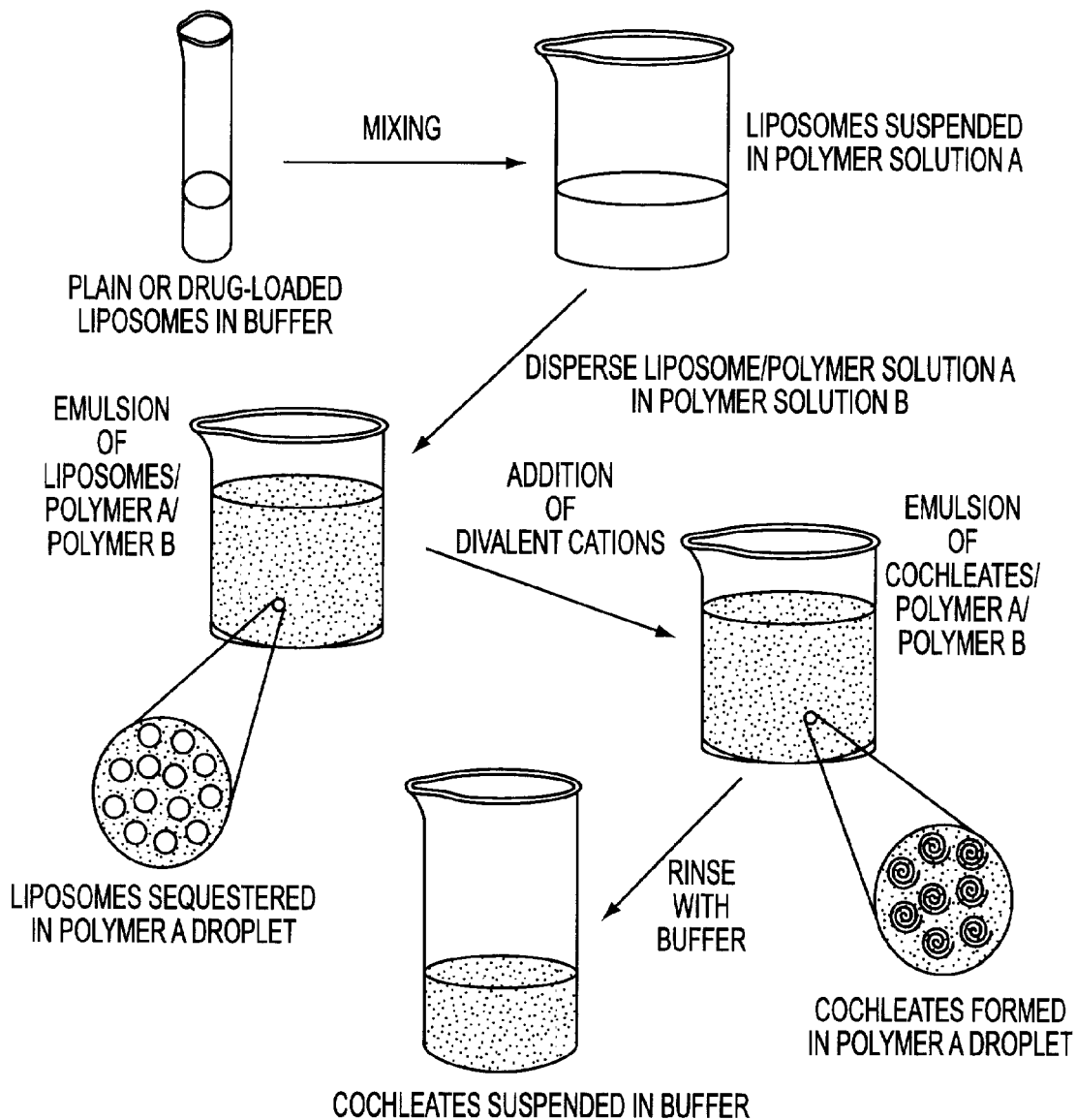
FIG. 1. Schematic of the process by which the hydrogel-isolated cochleates with or without drug are obtained.

The present invention provides a solution to achieve effective oral delivery of drugs by producing small-sized cochleates using a new process. The new approach is based on the incompatibility between two polymer solutions, both of which are aqueous. Aqueous two-phase systems of polymers are well used for protein purification due to a number of advantages such as freedom from the need for organic solvents, mild surface tension and the biocompatibility of aqueous polymers (see P. A. Albertsson in "Partition of cell particles and macromolecules", $3^{rd}$ edition, Wiley N.Y. 1986; and "Separation using aqueous Phase System" D. Fisher Eds, Plenum N.Y., 1989). It is known, for example, that large polar molecules such as proteins partition to a much higher concentration in a polymer phase with the physical characteristics similar to those of dextran than in a polymer phase with the physical characteristics similar to those of PEG (D. Forciniti, C. K. Hall, M. R. Kula, Biotechnol. Bioeng. 38, 986 1991).

According to the present invention there is provided a process for preparing small-sized, lipid-based cochleate particles and pharmaceutical preparations derived therefrom, comprising a pharmaceutical agent incorporated into the particles. The cochleate particles are formed of an alternating sequence of lipid bilayers/cation. The pharmaceutical agent is incorporated either in the lipid bilayers or in the interspace between the lipid bilayers. The process for preparing the small-sized cochleates comprises 1) preparing to suspension of small unilamellar liposomes or drug loaded liposomes, 2) mixing the liposome suspension with polymer A, 3) adding, preferably by injection, the liposome/Polymer A suspension into another polymer B in which polymer A is nonmiscible, leading to an aqueous two-phase system of polymers, 4) adding a solution of cation salt to the two-phase system of step 3, such that the cation diffuses into polymer B and then into the particles comprised of liposome/polymer A allowing the formation of small-sized cochleates, 5) washing the polymers out and resuspending the empty or drug-loaded cochleates into a physiological buffer or any appropriate pharmaceutical vehicle.

A lyophilization procedure can be applied and the lyophilized drug-cochleate complex can be filled into soft or hard gelatin capsules, tablets or other dosage form, for systemic, dermal or mucosal delivery.

This process leads to a small-sized particle with a narrow size range within the range that will allow oral delivery of drugs. The drugs partition into either or both lipid bilayers and interspace and the drug is released from the cochleate particles by dissociation of the particles in vivo. The resultant cochleate formulations allow an efficient oral delivery of drugs. An alternative route of administration can be intravenous, intranasal or by inhalation, intraocular, intravaginal or any other mucosal surfaces. Appropriate dosages are determinable by, for example, dose-response experiments in laboratory animals or in clinical trials and taking into account body weight of the patient, absorption rate, half-life, disease severity and the like. The number of doses, daily dosage and course of treatment may vary from individual to individual. Other delivery routes can be dermal or transdermal.

The first step of the new process of the present invention, which is the preparation of small liposomes, can be achieved by standard methods such as sonication or microfluidization or other related methods (see for example Liposome Technology, Liposome preparation and Related Techniques, Edited by Gregory Gregoriadis, Vol I, 2nd Edition, CRC Press, 1993).

The addition, preferably by injection, of polymer A/liposome suspension into polymer B can be achieved mechanically by using a syringe pump at an appropriate controlled rate, for example a rate of 0.1 ml/min to 50 ml/min and preferably at a rate of 1 to 10 ml/min.

The lipids of the present invention can do any non-toxic lipids and include, but are not limited to simple lipids which are found in animal and plant cell membranes. Preferably the lipid is a negatively charged lipid, more preferably a negatively charged phospholipid, and even more preferably those from the group of phosphatidylserine, phosphatidylinositol, phosphatidic acid, and phosphatidyl glycerol.

The polymers A and B of the present invention can be of any biocompatible polymer classes that can produce an aqueous two-phase system. For example, polymer A can be, but is not limited to, dextran 200,000–500,000, Polyethylene glycol (PEG) 3,400–8,000; polymer B can be, but is not limited to, polyvinylpyrrolidone (PVP), polyvinylalcohol (PVA), Ficoll 30,000–50,000, polyvinyl methyl ether (PVMB) 60,000–160,000, PEG 3,400–8,000. The concentration of polymer A can range from between 2–20% w/w as the final concentration depending on the nature of the polymer. The same concentration range can be applied for polymer B. Examples of suitable two-phase systems are Dextran/PEG, 5–20% w/w Dextran 200,000–500,000 in 4–10% w/w PEG 3,400–8,000; Dextran/PVP 10–20% w/w Dextran 200,000–500,000 in 10–20% w/w PVP 10,000–20,000; Dextran/PVA 3–15% w/w Dextran 200,000–500,000 in 3–15% w/w PVA 10,000–60,000; Dextran/Ficoll 10–20% w/w Dextran 200,000–500,000 in 10–20% w/w Ficoll 30,000–50,000; PEG/PVME 2–10% w/w PEG 3,500–35,000 in 6–15% w/w PVME 60,000–160,000.

The drug can be an organic molecule that is hydrophobic in aqueous media. The drug can be, but is not limited to, an antiviral, an anesthetic, an anti-infectious, an antifungal, an anticancer, an immunosuppressant, a steroidal anti-inflammatory, a non-steroidal anti-inflammatory, a tranquilizer or a vasodilatory agent. Examples include Amphotericin B, acyclovir, adriamycin, cabamazepine, melphalan, nifedipine, indomethacin, naproxen, estrogens, testosterones, steroids, phenytoin, ergotamines, cannabinoids rapamycin, propanidid, propofol, alphadione, echinomycine, miconazole nitrate, teniposide, taxol, and taxotere.

The drug can be a polypeptide such as cyclosporin, angiotensin 1, II and III, enkephalins and their analogs, ACTH, anti-inflammatory peptides I, II, III, bradykinin, calcitonin, b-endorphin, dinorphin, leucokinin, leutinizing hormone releasing hormone (LHRH), Insulin, neurokinins, somatostatin, substance P, thyroid releasing hormone (TRH) and vasopressin.

The drug can be an antigen, but is not limited to a protein antigen. The antigen can also be a carbohydrate or DNA. Examples of antigenic proteins include envelope glycoproteins from influenza or Sendai viruses, animal cell membrane proteins, plant cell membrane proteins, bacterial membrane proteins and parasitic membrane protein.

The antigen is extracted out from the source particle, cell, tissue, or organism by known methods. Biological activity of antigens need not be maintained. However, in some instances (e.g., where a protein has membrane fusion or ligand binding activity or a complex conformation which is recognized by the immune system), it is desirable to maintain the biological activity. In these instances, an extraction buffer containing a detergent which does not destroy the biological activity of the membrane protein is used. Suitable detergents include ionic detergents such as cholate salts, deoxycholate salts and the like or heterogeneous polyoxyethylene detergents such as Tween, BRIG or Triton.

Utilization of this method allows reconstitution of antigens, more specifically proteins, into the liposomes with retention of biological activities, and eventually efficient association with the cochleates. This avoids organic solvents, sonication, or extreme pH, temperature, or pressure all of which may have an adverse effect upon efficient reconstitution of the antigen in a biologically active form.

Hydrogel-isolated cochleates can include multiple antigenic molecules, biologically relevant molecules or drug formularies as appropriate.

The formation of small-sized cochleates (with or without drugs) is achieved by adding a positively charged molecule to the aqueous two-phase polymer solution containing liposomes. In the above procedure for making cochleates, the positively charged molecule can be a polyvalent cation and more specifically, any divalent cation that can induce the formation of a cochleate. In a preferred embodiment, the divalent cations include $Ca^{++}$, $Zn^{++}$, $Ba^{++}$ and $Mg^{++}$ or other elements capable of forming divalent ions or other structures having multiple positive charges capable of chelating and bridging negatively charged lipids. Addition of positively charged molecules to liposome-containing solutions are also used to precipitate cochleates from the aqueous solution.

To isolate the cochleate structures and to remove the polymer solution, cochleate precipitates are repeatedly washed with a buffer containing a positively charged molecule, and more preferably, a divalent cation. Addition of a positively charged molecule to the wash buffer ensures that the cochleate structures are maintained throughout the wash step, and that they remain as precipitates.

The medium in which the cochleates are suspended can contain salt such as sodium chloride, sodium sulfate, potassium sulfate, ammonium sulfate, magnesium sulfate, sodium carbonate. The medium can contain polymers such as Tween 80 or BRIG or Triton. The drug-cochleate is made by diluting into an appropriate pharmaceutically acceptable carrier (e.g., a divalent cation-containing buffer).

The cochleate particles can be enteric. The cochleate particles can be placed within gelatin capsules and the capsule can be enteric coated.

In the pharmaceutical preparations of the present invention certain hydrophobic materials can be added to provide enhanced absorption properties for oral delivery of drugs. These materials are preferably selected from the group consisting of long chain carboxylic acids, long chain carboxylic acid esters, long chain carboxylic acid alcohols and mixtures thereof. The hydrophobic materials can be added either initially to the lipid prior to the formation of liposomes or in a later step in the form of a fat vehicle such as an emulsion.

The skilled artisan can determine the most efficacious and therapeutic means for effecting treatment practicing the instant invention. Reference can also be made to any of numerous authorities and references including, for example, "Goodman & Gillman's, The Pharmaceutical Basis for Therapeutics", ($6^{th}$ Ed., Goodman et al., eds., MacMillan Publ. Co., New York, 1980). The invention will now be described by examples which are not to be considered as limiting the invention. In the examples, unless otherwise indicated, all ratios, percents and amounts are by weight.

EXAMPLES

Example 1

Preparation of Empty Hydrogel-isolated Cochleates Precipitated with Calcium

Step 1: Preparation of small unilamellar vesicles from dioleoylphosphatidyl serine.

A solution of dioleoyl phosphatidyl serine (DOPS, Avanti Polar Lipids, Alabaster, Ala., USA) in chloroform (10 mg/ml) was placed in a round-bottom flask and dried to a film using a Buchi rotavapor at 35° C. The rotavapor was sterilized by flashing nitrogen gas through a 0.2 μm filter. The following steps were carried out in a sterile hood. The dried lipid film was hydrated with de-ionized water at the concentration of 10 mg lipid/ml. The hydrated suspension was purged and sealed with nitrogen, then sonicated in a cooled bath sonicator (Laboratory Supplies Com., Inc.). Sonication was continued (for several seconds to several minutes depending on lipid quantity and nature) until the suspension became clear (suspension A) and there were no liposomes apparently visible under a microscope with a 100× lens. Laser light scattering (weight analysis, Coulter N4 Plus) indicates that the mean diameter is 35.7±49.7 nm.

Step 2 : Preparation of hydrogel isolated cochleates

The liposome suspension obtained in step 1 was then mixed with 40 % w/w dextran-500,000 (Sigma) in a suspension of 3/1 v/v Dextran/liposome. This mixture was then injected via a syringe into 15% w/w PEG-8,000 (Sigma) [PEG 8000/(suspension A)] under magnetic stirring to result in suspension B. The rate of the stirring was 800–1,000 rpm. A $CaCl_2$ solution (100 mM) was added to the suspension to reach the final concentration of 1 mM.

Figure 2A:
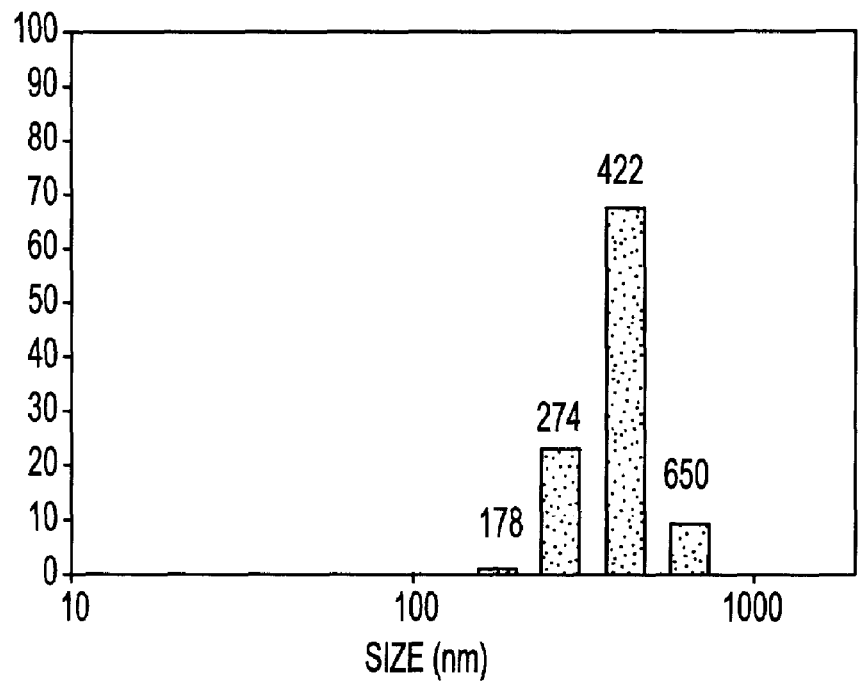
FIGS. 2A and 2B. Particle size distribution (weight analysis) of hydrogel isolated cochleates either loaded with amphotericin B (AmB) (FIG. 2A) or empty (FIG. 2B) as measured by laser light scattering.
Figure 2B:
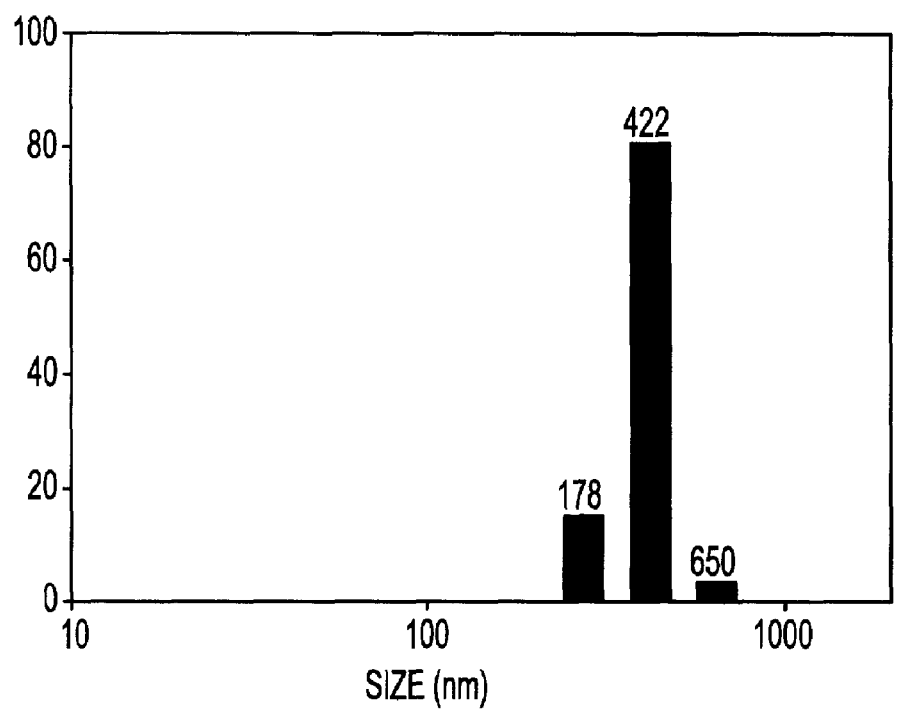

Stirring was continued for one hour, then a washing buffer containing 1 mM $CaCl_2$ and 150 mM NaCl was added to suspension B at the volumetric ratio of 10:1. The suspension was vortexed and centrifuged at 3000 rpm, 2–4° C., for 30 min. After the supernatant was removed, additional washing buffer was added at the volumetric ratio of 5:1, followed by centrifugation under the same conditions. A schematic of this new process of obtaining cochleates is detailed in FIG. 1. The resulted pellet was reconstituted with the same buffer to the desired concentration. Laser light scattering (weight analysis, Coulter N4 Plus) indicates that the cochleates mean diameter is 407.2±85 nm (FIG. 2b).

Example 2

Preparation of Amphotericin B Loaded Hydrogel Isolated Cochleates Precipitated with Calcium Step 1: Preparation of small unilamellar AmB-loaded vesicles from dioleoylphosphatidyl serine.

A mixture of dioleoyl phosphatidyl serine (DOPS, Avanti Polar Lipids, Alabaster, Ala., USA) in chloroform (10 mg/ml) and AmB in methanol (0.5mg/ml) at a molar ratio of 10:1 was placed in a round-bottom flask and dried to a film using a Buchi rotavapor at 40° C. The rotavapor was sterilized by flashing nitrogen gas through a 0.2 μm filter. The following steps were carried out in a sterile hood. The dried lipid film was hydrated with de-ionized water at the concentration of 10 mg lipid/ml. The hydrated suspension was purged and sealed with nitrogen, then sonicated in a cooled bath sonicator (Laboratory Supplies Comp., Inc.). Sonication was continued (for several seconds to several minutes depending on lipid quantity and nature) until the suspension became clear yellow (suspension A) and there were no liposomes apparently visible under a microscope with a 100× lens. Laser light scattering (weight analysis, Coulter N4 Plus) indicated that the mean diameter was 407.1±119 nm.

Step 2: Preparation of, AmB-loaded, hydrogel isolated cochleates

The liposome suspension obtained in step 1 was then mixed with 40 % w/w dextran-500,000 (Sigma) in a suspension of 3/1 v/v Dextran/liposome. This mixture was then injected via a syringe into 15% w/w PEG-8,000 (Sigma)

[PEG 8000/(suspension A)] under magnetic stirring to result in suspension B. The rate of the stirring was 800–1,000 rpm. A CaCl$_2$ solution (100 mM) was added to the suspension to reach the final concentration of 1 mM.

Stirring was continued for one hour, then a washing buffer containing 1 mM CaCl$_2$ and 150 mM NaCl was added to suspension B at the volumetric ratio of 10:1. The suspension was vortexed and centrifuged at 3000 rpm, 2–4° C., for 30 min. After the supernatant was removed, additional washing buffer was added at the volumetric ratio of 5:1, followed by centrifugation under the same conditions. A schematic of this new process of obtaining cochleates is detailed in FIG. 1. The resulting pellet was reconstituted with the same buffer to the desired concentration. Laser light scattering (weight analysis, Coulter N4 Plus) indicate that the AmB-cochleates mean diameter was 407.3±233.8 nm (FIG. 2A).

Example 3

Preparation of Empty Hydrogel Isolated-cochleates Precipitated with Zinc

Step 1: Preparation of small unilamellar vesicles from dioleoylphosphatidyl serine.

A solution of dioleoyl phosphatidyl serine (DOPS, Avanti Polar Lipids, Alabaster, Ala., USA) in chloroform (10 mg/ml) was placed in a round-bottom flask and dried to a film using a Buchi rotavapor at 35° C. The rotavapor was sterilized by flashing nitrogen gas through a 0.2 µm filter. The following steps were carried out in a sterile hood. The dried lipid film was hydrated with de-ionized water at the concentration of 10 mg lipid/ml. The hydrated suspension was purged and sealed with nitrogen, then sonicated in a cooled bath sonicator (Laboratory Supplies Comp., Inc.). Sonication was continued (for several seconds to several minutes depending on lipid quantity and nature) until the suspension became clear (suspension A) and there were no liposomes apparently visible under a microscope with a 100× lens. Laser light scattering (weight analysis, Coulter N4 Plus) indicated that the mean diameter was 35.7±49.7 nm.

Step 2: Preparation of hydrogel isolated cochleates

The liposome suspension obtained in step 1 was then mixed with 40 % w/w dextran-500,000 (Sigma) in a suspension of 3/1 v/v Dextran/liposome. This mixture was then injected via a syringe into 15% w/w PEG-8,000 (Sigma) [PEG 8000/(suspension A)] under magnetic stirring to result in suspension B. The rate of the stirring was 800–1,000 rpm. A ZnCl$_2$ solution (100 mM) was added to the suspension to reach the final concentration of 1 mM.

Stirring was continued for one hour, then a washing buffer containing 1 mM ZnCl$_2$ and 150 mM NaCl was added to suspension B at the volumetric ratio of 10:1. The suspension was vortexed and centrifuged at 3000 rpm, 2–4° C., for 30 min. After the supernatant was removed, additional washing buffer was added at the volumetric ratio of 5:1, followed by centrifugation under the same conditions. A schematic of this new process of obtaining cochleates is detailed in FIG. 1. The resulted pellet was reconstituted with the same buffer to the desired concentration. Laser light scattering (weight analysis, Coulter N4 Plus) confirmed the formation of small cochleates.

Example 4

Preparation of Amphotericin B loaded hydrogel isolated cochleates precipitated with Zinc Step 1 : Preparation of small unilamellar AmB-loaded vesicles from dioleoylphosphatidyl serine.

A mixture of dioleoyl phosphatidyl serine (DOPS, Avanti Polar Lipids, Alabaster, Ala., USA) in chloroform (10 mg/ml) and AmB in methanol (0.5 mg/ml) at a molar ratio of 10:1 was placed in a round-bottom flask and dried to a film using a Buchi rotavapor at 40° C. The rotavapor was sterilized by flashing nitrogen gas through a 0.2 µm filter. The following steps were carried out in a sterile hood. The dried lipid film was hydrated with de-ionized water at the concentration of 10 mg lipid/ml. The hydrated suspension was purged and sealed with nitrogen, then sonicated in a cooled bath sonicator (Laboratory Supplies Corn., Inc.). Sonication was continued (for several seconds to several minutes depending on lipid quantity and nature) until the suspension became clear yellow (suspension A) and there were no liposomes apparently visible under a microscope with a 100× lens. Laser light scattering (weight analysis, Coulter N4 Plus) indicate that the mean diameter was 407.1±119 nm.

Step 2: Preparation of, AmB-loaded, hydrogel isolated cochleates

The liposome suspension obtained in step 1 was then mixed with 40 % w/w dextran-500,000 (Sigma) in a suspension of 3/1 v/v Dextran/liposome. This mixture was then injected via a syringe into 15% w/w PEG-8,000 (Sigma) [PEG 8000/(suspension A)] under magnetic stirring to result in suspension B. The rate of the stirring was 800–1,000 rpm. A ZnCl$_2$ solution (100 mM) was added to suspension to reach the final concentration of 1 mM.

Stirring was continued for one hour, then a washing buffer containing 1 mM ZnCl$_2$ and 150 mM NaCl was added to the suspension B at the volumetric ratio of 10:1. The suspension was vortexed and centrifuged at 3000 rpm, 2–4° C., for 30 min. After the supernatant was removed, additional washing buffer was added at the volumetric ratio of 5:1, followed by centrifugation under the same conditions. A schematic of this new process of obtaining cochleates is detailed in FIG. 1. The resulted pellet was reconstituted with the same buffer to the desired concentration. Laser light scattering (weight analysis, Coulter N4 Plus) confirmed the formation of small AmB-Zn-cochleates.

Example 5

Microscopic observation of Hydrogel-isolatedcochleates

Optical microscopic study was performed stepwise alone with the preparation procedure in order to gain some mechanistic details of the hydrogel-isolated cochleates formation.

Figure 3A:
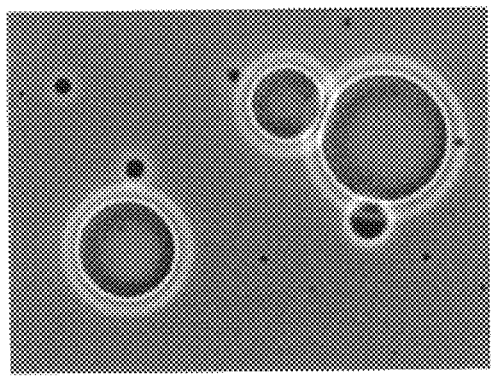
FIGS. 3A and 3B) Microscopic images of a mixture of liposomes in dextran dispersed into PEG gel solution. The small black dots are dextran particles formed by dispersing the dextran phase in the PEG phase. The large open circles are formed by fusion of small dextran particles. Partition of liposomes favors the dextran phase as indicated by the yellow color of AmB. 3B) Microscopic images of the sample shown in FIG. 3A after treatment with $CaCl_2$ solution. The black objects in circles, indicated by an arrow, are cochleates formed by the addition of $Ca^{2+}$ ions.
Figure 3B:
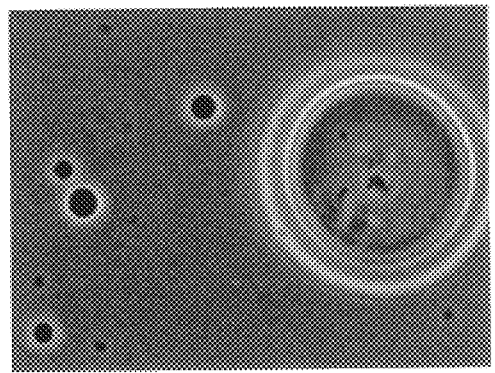
Figure 4A:
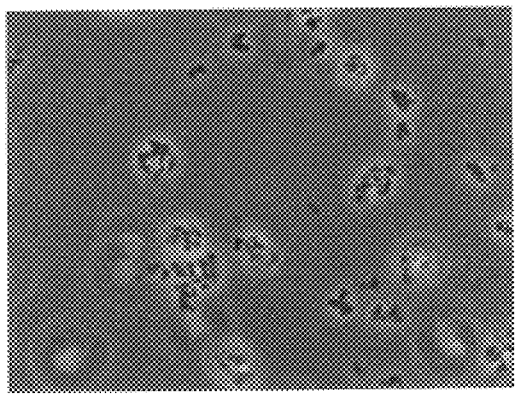
FIGS. 4A–4F) Microscopic images of the sample shown in FIGS. 3A and 3B after washing with a buffer containing 1 mM $CaCl_2$ and 100 mM NaCl. Aggregates are formed by the Cochleate particles. 4B) Suspension shown in FIG. 4A following the addition of EDTA. Cochleate particles opened to liposomes with a diameter of 1–2 microns, indicating the intrinsic size of the cochleate particles is in sub-micron range. 4C) AmB hydrogel isolated-cochleates precipitated with zinc according to the procedure described in Example 4. 4D) Cochleates displayed in FIG. 4C after treatment with EDTA. 4E) Empty hydrogel isolated-cochleates precipitated with zinc according to the procedure described in Example 3. 4F) cochleates displayed in 4F after treatment with EDTA.
Figure 4B:
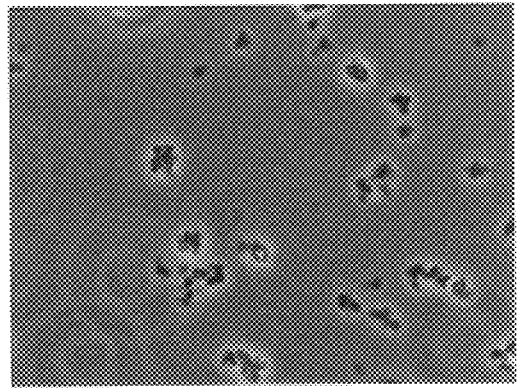
Figure 4C:
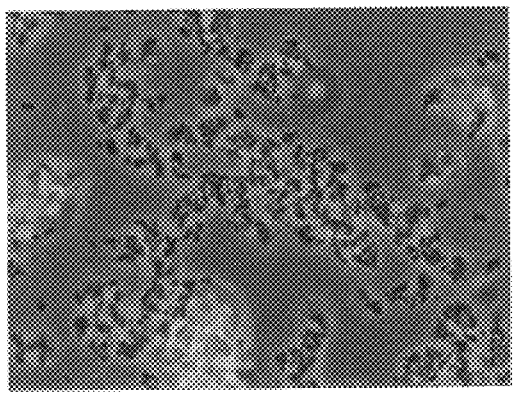
Figure 4D:
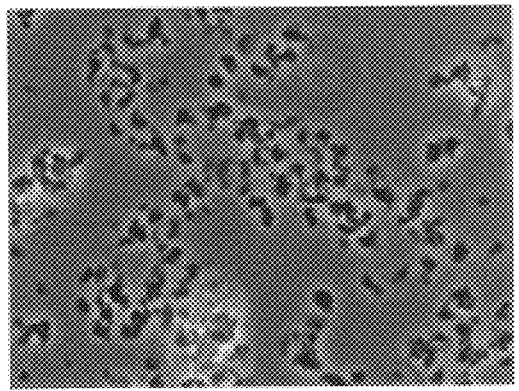
Figure 4E:
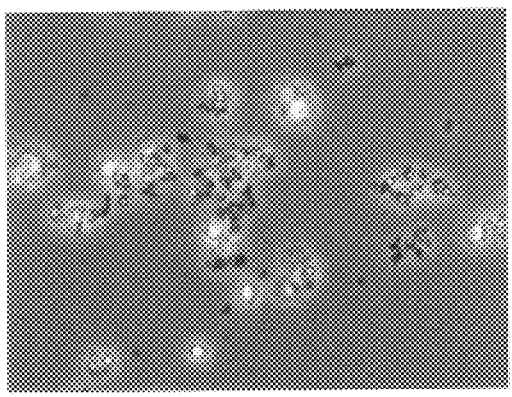
Figure 4F:
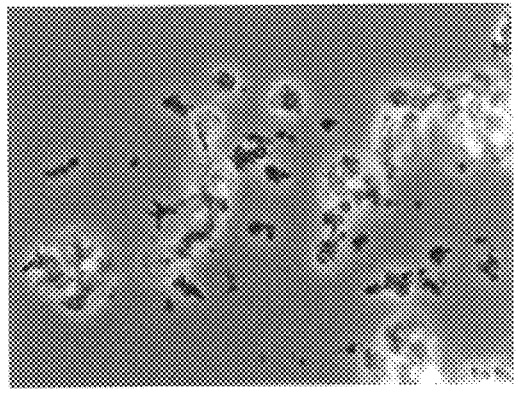
Figure 5:
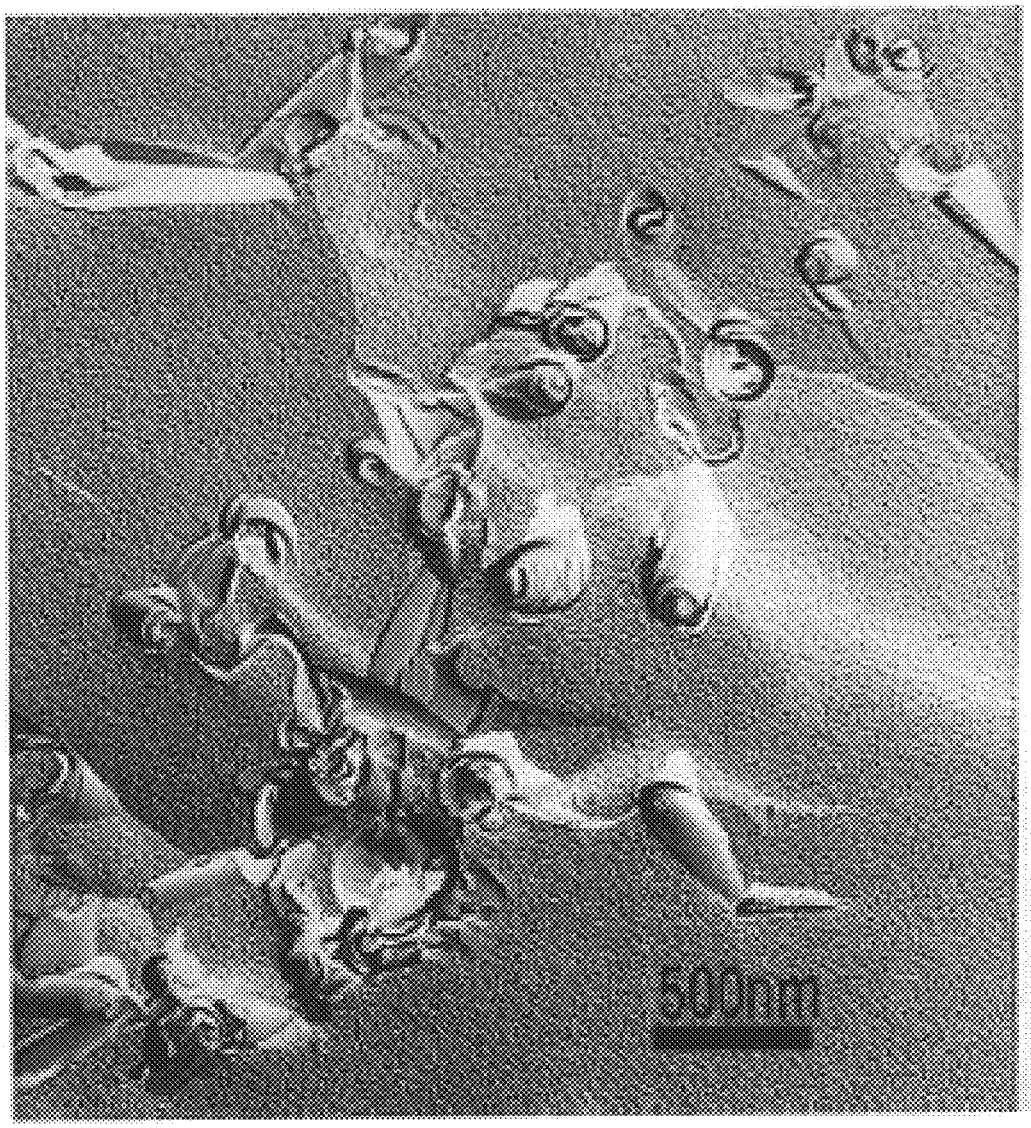
FIG. 5. Micrographs of hydrogel-isolated cochleates after freeze fracture.

The microscopic images seen in FIGS. 3A,B and 4A–F show the morphological changes at each preparation step of AmB loaded nanocochleates precipitated with Ca$^{2+}$ ions. When the AmB/liposome-dextran mixture was dispersed into PEG solution, phase separation resulted as shown by FIG. 3A. Partition of the liposomes favored the dispersed dextran phase as indicated by a yellow color of AmB. This partitioning ensures that liposomes are isolated in each dextran particles. Addition of Calcium ions into the continued phase (PEG) resulted in formation of precipitates in the dispersed phase. As the final product, small needle-shape cochleates were formed and observed under the microscope, these cochleates opened into unilamellar vesicles upon addition of EDTA and chelation of the calcium (FIGS. 4A,B). The needle-shaped morphology was confirmed by scanning electron microscopy after freeze-fracture (FIG. 5). Similar microscopic images were obtained for empty and AmB-Zn-precipitated hydrogel isolate-dcochleates (FIGS. 4C,D) and empty Zn-precipitated hydrogel isolated-cochleate (FIG. 4E,F)

Example 6

Antifungal Activity of hydrogel isolated cochleates loaded with Amphotericin B, in vitro

Growth Inhibition of Candida albicans

An in vitro yeast susceptibility assay was performed comparing the inhibitory and lethal effects of AmB-cochleates, AmBisomes (liposomal formulation of AmB) and AmB/DMSO. Five colonies of freshly growing Candida albicans were selected from a YPD agar plate (from a 48 hour culture) and added to 2 ml of 2× YPD broth, pH 5.7. The $OD_{590}$ of this stock culture was measured and the yeast density was adjusted to $OD_{590=0.1}$ and subsequently plated onto a 96 well plate.

Figure 6:
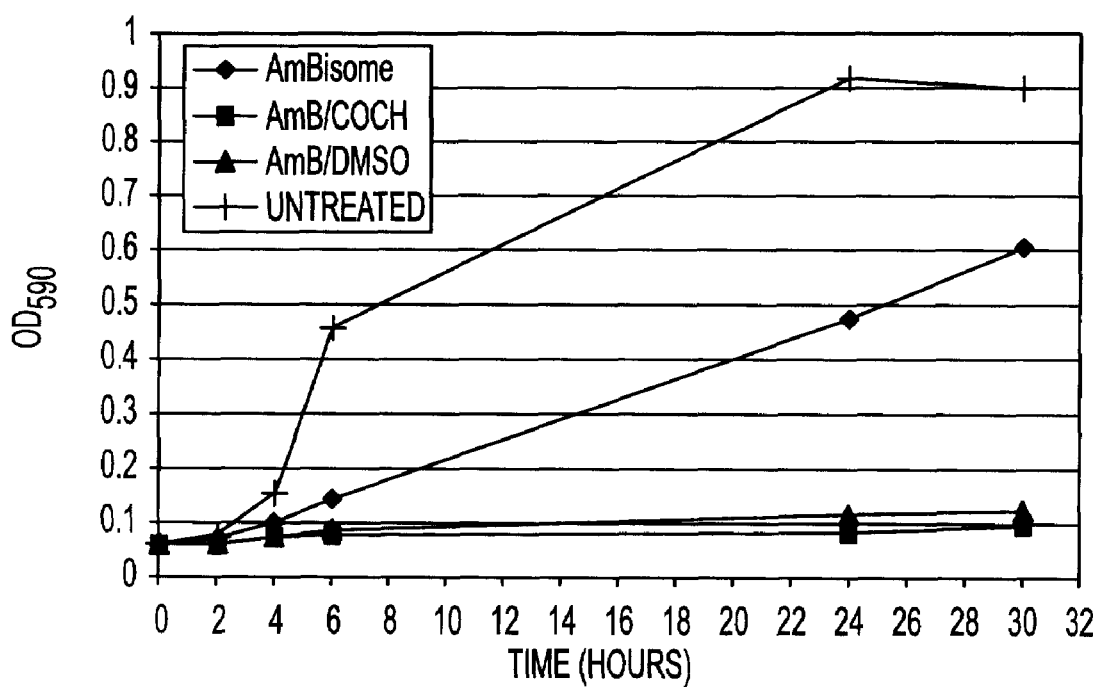
FIG. 6. Growth inhibition of *Candida albicans* by hydrogel-isolated cochleates loaded with AniB at 0.625 µg AmB/ml. Comparison is made to AmB in DMSO and AmBisome$^R$.

AmB/cochleates, AmB/DMSO and AmBisomes were added to 96 well plates to a final concentration of 0.078, 0.156, 0.3125, 0.625, 1.25 and 2.5 μg/ml of AmB. The 96 well plates were incubated at 37° C. with gentle shaking and cell density was measured on a 96 well plate reader (Molecular Devices Spectramax 340) at 0, 2, 4, 6, 24 and 30 hours. FIG. 6 shows that AmB-cochleates have a greater growth inhibitory effect than AmBisomes (liposomal formulation of AmB).

Fungicidal effect of hydrogel isolated cochleates loaded with Amphotericin B.

Aliquots of yeast cells (50 μl) were removed from the 96 well plates and serially diluted (up to 1:10000 for plating onto agar plates) and counted using a hemocytometer. Fifty μl of the diluted yeast cells were plated onto YPD agar plates and incubated for 24 hours at 37° C. Yeast colonies were counted using a BioRad Fluor-S Multi-Imager equipped with Quanitity One™ software.

Figure 7:
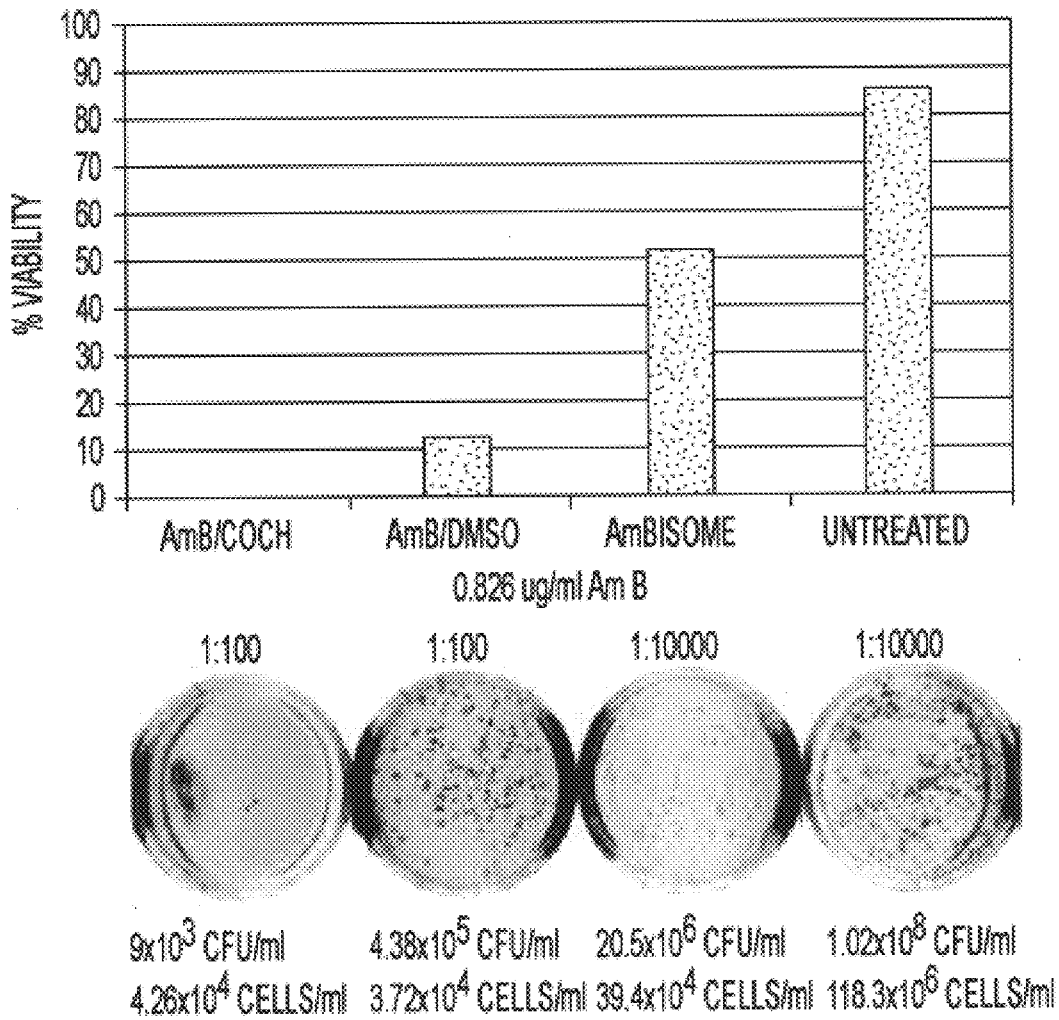
FIG. 7. Effect of hydrogel-isolated cochleates on the viability of *Candida albicans* after 30 hours.

Triplicate data from spectrophotometric analysis of duplicate 96 well plates shows that AmB-cochleates have a fungicidal effect on *Candida albicans* greater than AmB/DMSO and AmBisome at a concentration of 0.625 μg AmB/ml. This trend was observed after 30 hours with AmB concentrations ranging from 0.3125 to 1.25 μg/ml (data not shown). The yeast cells treated with AmBisome, AmB/DMSO and AmB/cochleates (0.625 ug AmB/ml) were also examined for the ratio of colony forming units to total cell number after 30 hours of incubation. The results show that the AmB/cochleates had the greatest lethal effect on the yeast cells compared to the other antifungal agents tested. There was nearly 0% yeast viability after treatment with the AmB-cochleates and 12% yeast viability after treatment with AmB/DMSO. The AmBisome was not as effective, resulting in 52% yeast viability (FIG. 7).

Example 7

Oral delivery of AmB mediated by hydrogel isolated cochleates loaded with AmB.

Single dose regime

Oral availability of the hydrogel isolated cochleates loaded with AmB has been examined by intragastric administration of the formulation of example 2 to overnight fasted, C57BL16 mice (20–23g). One tenth ml of the formulation at the dose of 10 mg/kg was administrated to 9 mice. Three mice from each group were sacrificed 6 and 24 hrs post administration, respectively, followed by analysis of AmB level in organs and tissues.

Tissue and blood samples were processed as follows: tissues were diluted 1/20 or 1/10 by addition of extraction solvent ($H_2O$ 35%, methanol 10%, ethanol 55% w/w/w nv/v/v) and homogenized with a Ultra-Turrex® device. And 0.5 ml aliquot was taken, sonicated for 1 min and centrifuged at 7260 rpm for 12 min at 4° C. Supernatant was transferred to a HPLC microvial and 30 μl injected on a C-18, 3.9×150 mm, 4 μm particle sized analytical column with a flow rate of 0.5 ml, at 40° C. Concentration of AmB detected at 408 nm was calculated with the help of an external calibration curve.

Figure 8A:
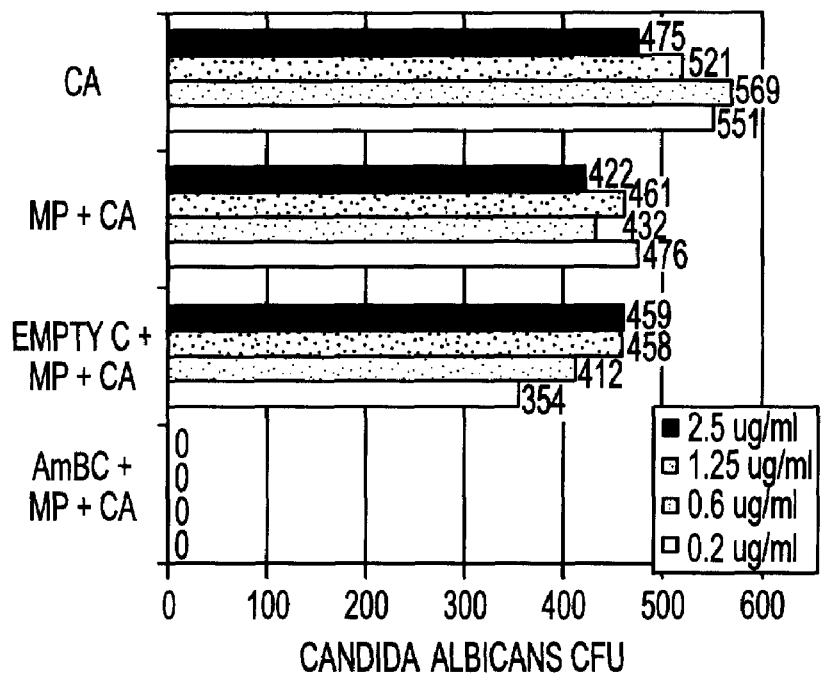
FIG. 8. Time profile tissue concentration of AmB after single dose administration of hydrogel-isolated cochleates loaded with AmB.
Figure 8B:
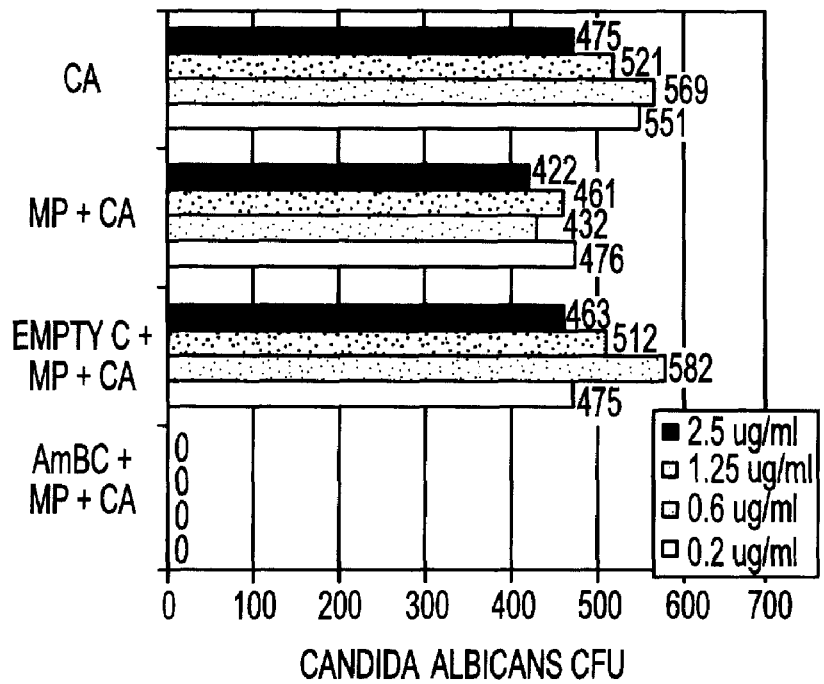

FIG. 8 shows the time profile of AmB in the tissues over a period f time of 24 hrs. Although only three time points are plotted, accumulation in key tissues (liver, lungs, spleen and kidneys) can be seen.

Multiple dose regime

Figure 9:
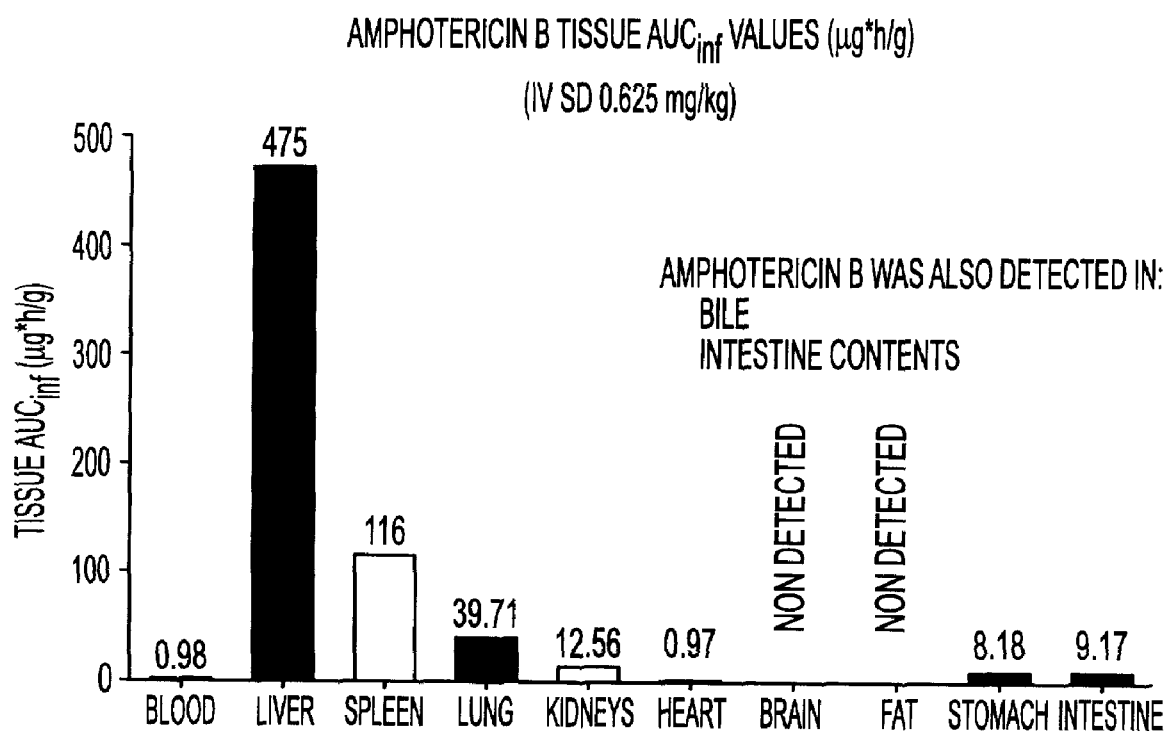
FIG. 9. AmB tissue level 24 hrs after single dose and 24 hrs after a multiple dose regime.

Two other groups of mice received a 10 mg/kg oral multiple dose regime for ten days and one group was sacrificed 24 hrs after last dose and the other group 20 days after the last dose received. At the predetermined time points mice were anesthetized, sacrificed and dissected for tissue collection. Tissues were processed as in single dose regime and AmB level determined by HPLC. Results from 24 h after the $_{10}$th dose are depicted in FIG. 9 and show that hydrogel isolated cochleates allow the delivery of AmB from the gastrointestinal tract at therapeutic levels.

What is claimed:

1. A method for producing a small-sized, lipid-based cochleate which comprises the steps of:
   a) preparing small, unilamellar liposomes;
   b) mixing the liposome suspension with polymer A;
   c) adding the liposome/polymer A suspension into a solution comprising polymer B, wherein polymer A and polymer B are nonimiscible, thereby creating a two-phase polymer system;
   d) adding a solution comprised of a positively charged molecule to the two-phase polymer system; and
   e) removing excess polymer by centrifugation.

2. The method of claim 1, wherein the addition of liposome/polymer A suspension is done by injection.

3. The method of claim 1, wherein the liposome is comprised of negatively charged lipid.

4. The method of claim 3, wherein the negatively charged lipid is comprised of phosphatidylserine.

5. The method of claim 1, wherein polymer A is at least one member selected from the group consisting of dextran and polyethylene glycol.

6. The method of claim 5, wherein polymer A ranges in concentration from 2–20% w/w.

7. The method of claim 1, wherein polymer B is at least one member selected from the group consisting of polyvinylpyrrolidone, polyvinylalcohol, Ficoll, polyvinyl methyl ether, and polyethylene glycol.

8. The method of claim 7, wherein polymer B ranges in concentration from 2–20% w/w.

9. The method of claim 1, wherein the two-phase polymer solution is at least one member selected from the group consisting of Dextran/polyethylene glycol, Dextran/polyvinylpyrrolidone, Dextran/poly-vinylalcohol, Dextran/Ficoll, and polyethylene glycol/polyvinyl methyl ether.

10. The method of claim 1, wherein the positively charged molecule is comprised of a cationic salt.

11. The method of claim 10, wherein the cationic salt is $CaCl_2$ or $ZnCl_2$.

12. The method of claim 1, wherein the lipid cochleate is of a particle size of less than one micron.

13. A drug cochleate composition prepared according to the method of claim 1 comprising:
   a) a drug component;
   b) a negatively charged lipid; and
   c) a divalent cation component,
   wherein the particle size of the drug cochleate is less than one micron.

14. The composition of claim 13, wherein the drug is at least one member selected from the group consisting of an antiviral, an anesthetic, an anti-infectious, an antifungal, an anticancer, an immunosuppressant, a steroidal anti-inflammatory, a non-steroidal anti-inflammatory, a tranquilizer, and a vasodilatory agent.

15. The composition of claim 14, wherein the drug is at least one member selected from the group consisting of Amphotericin B, acyclovir, adriamycin, cabamazepine, melphalan, nifedipine, indomethacin, naproxen, estrogens, testosterones, steroids, phenytoin, ergotamines, cannabinoids, rapamycin, propanidid, propofol, alphadione, echinomycine, miconazole nitrate, teniposide, taxol, and taxotere.

16. The composition of claim 13, wherein the drug is selected from the group consisting of a polypeptide or an antigen.

17. A method of treatment comprising administering to a host in need of treatment the drug cochleate composition of claim 13 wherein the particle size of the drug cochleate is less than one micron.

18. The method of claim 17, wherein the drug is at least one member selected from the group consisting of an antiviral, an anesthetic, an anti-infectious, an antifungal, an anticancer, an immunosuppressant, a steroidal anti-inflammatory, a non-steroidal anti-inflammatory, a tranquilizer, and a vasodilatory agent.

19. The method of claim 18, wherein the drug is at least one member selected from the group consisting of Aniphotericin B, acyclovir, adriamycin, cabamazepine, melphalan, nifedipine, indomethacin, naproxen, estrogens, testosterones, steroids, phenytoin, ergotamines, cannabinoids, rapamycin, propanidid, propofol, alphadione, echinomycine, miconazole nitrate, teniposide, taxol, and taxotere.

20. The method of claim 17, wherein the drug at least one member selected from the group consisting of a polypeptide and an antigen.

21. The method of claim 17, wherein the administering is by mucosal or systemic route.

22. The method of claim 17, wherein the mucosal route is oral, intranasal, intraocular, intraanal, intravaginal or by inhalation.

23. The method of claim 22, wherein the administering is by an oral route.

24. The method of claim 17, wherein the systemic route is intravenous, intramuscular, subcutaneous, transdermal, or intradermal.

25. The method of claim 17, wherein the drug is a biologically relevant molecule.

26. A pharmaceutical composition comprising the drug cochleate composition of claim 13 and a pharmaceutically effective carrier.

* * * * *